US006615839B2

(12) United States Patent
Eichman

(10) Patent No.: US 6,615,839 B2
(45) Date of Patent: Sep. 9, 2003

(54) SURGICAL METHOD FOR THE DELIVERY OF SALIVA-BORNE ANTIBODIES TO THE BLOOD STREAM FOR THE TREATMENT OF INFECTIOUS DISEASES

(76) Inventor: Roger Keith Eichman, 223 Griffins Pt. Rd., Nordland, WA (US) 98358

( * ) Notice: Subject to any disclaimer, the term of this patent is extended or adjusted under 35 U.S.C. 154(b) by 0 days.

(21) Appl. No.: 09/972,171

(22) Filed: Oct. 3, 2001

(65) Prior Publication Data

US 2003/0062053 A1 Apr. 3, 2003

(51) Int. Cl.[7] ............................................. A61B 19/00
(52) U.S. Cl. ...................................................... 128/898
(58) Field of Search .......................................... 128/898

(56) References Cited

U.S. PATENT DOCUMENTS 4,839,342 A * 6/1989 Kaswan ....................... 514/11
6,022,847 A * 2/2000 Sheppard ...................... 514/2

* cited by examiner

Primary Examiner—Corrine McDermott
Assistant Examiner—Thomas J Sweet

(57) ABSTRACT

The invention is a low cost means to use the patient's own antibodies against an infectious disease such as a HIV virus infection by surgically shunting the naturally-occurring saliva-borne antibodies into the patient's bloodstream. To do this, a small incision is made in the central portion of the cheek near an area where the parotid duct and a blood vessel are in close proximity. This area is located using a light source. Then the parotid saliva duct is cut and attached to a vein such that the saliva flows into and mixes with the blood. The portion of the duct leading to the mouth is sealed off, while the portion leading to the salivary gland is temporarily left open. The parotid blood vessel is then cut and a surgical tee is inserted. The parotid duct is attached onto the perpendicular outlet of the surgical tee and the outlet of the parotid duct thereby linking the blood vessel and the parotid salivary duct.

8 Claims, 5 Drawing Sheets

SURGICAL METHOD FOR THE DELIVERY OF SALIVA-BORNE ANTIBODIES TO THE BLOOD STREAM FOR THE TREATMENT OF INFECTIOUS DISEASES

FIELD OF INVENTION

The present invention relates generally to a surgical method for the delivery of saliva-borne antibodies produced by the body to the blood stream of the patient for the treatment of blood-borne infectious diseases such as the HIV virus.

BACKGROUND OF THE INVENTION

Since recorded history, mankind has been attacked by infections diseases. The most recent disease to each monumental proportions is AIDS. AIDS was not formally identified as a disease until 1981. The human body has built-in mechanisms to handle the invasion by bacteria and viruses such as the HIV virus which causes AIDS.

The uniqueness of the HIV virus is that it attacks the immune system itself. Since AIDS was identified, many forms of treatment have been tried. To date, most treatments involve large doses of medication aimed at either attacking the HIV virus or bolstering the body's immune system. These treatments are, as a general rule, extremely expensive and have only been able to delay, at best, the onset of AIDS. The expense is so high that the chemo treatment's availability has been limited to the areas that have the highest economic income.

In rare cases, there has been the incidence of survival of a person infected with the HIV virus who has shown no effects of the disease. One theory that attempts to explain these phenomena is there may have been a mixing of saliva with the blood.

Guy's, King's and St. Thomas' Dental and Medical Schools, London, S. H. Kazmi et al has stated that saliva has demonstrated the ability to inhibit the replication of the HIV-1 in vitro. They quote studies that indicate that the factors that are responsible for the anti-HIV activity in saliva are from the effect of mucins (MG2), secretory leukocyte protease inhibitor (SLPI), cystatins, proline rich proteins, and lactoferrin.

Sialochemists know a great deal about saliva. It is not only sterile, but it is well recognized that saliva has antimicrobial and antifungal properties. The average person produces 1.5 liters of saliva each day. This amount of saliva produced, of course, varies with several factors. For example, diet, age, AIDS itself, other medical conditions such as diabetes, and whether you are standing, eating, or sitting can each influence the amount produced. Since the HIV virus and other infectious diseases are spreading worldwide, and a naturally-produced substance by the body itself is available to use to attack the deadly virus, it should be used to fight that disease.

In certain regions of the world today, as much as 35% of the population has been infected with the HIV virus. It is, therefore, necessary to find a means to make the maximum possible use of the body's own defense mechanisms to battle the HIV virus in a cost-effective way. This is possible with the instant invention.

SUMMARY OF THE INVENTION

The instant invention solves the problem of expense by utilizing the body's own naturally-produced antibodies to attack the infection directly in the bloodstream.

A small incision is made in the central portion of the cheek near an area where the parotid duct and a blood vessel are in close proximity. This area is located using a light source. Then the parotid saliva duct is cut and attached to a vein such that the saliva flows into and mixes with the blood. The portion of the duct leading to the mouth is sealed off while the portion leading from the salivary gland is temporarily left open. The parotid blood vessel is then cut and a surgical tee is inserted. The perpendicular outlet of the surgical tee is connected to the outlet of the parotid duct, thereby linking the blood vessel and the parotid saliva supply duct. This allows for the introduction of saliva which carries antibodies directly into the blood stream. Saliva itself assists in the operation in that it has an anti-clotting effect.

The subject matter of the present invention is particularly pointed out and distinctly claimed in the concluding portion of the specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENTS

Figure 1:
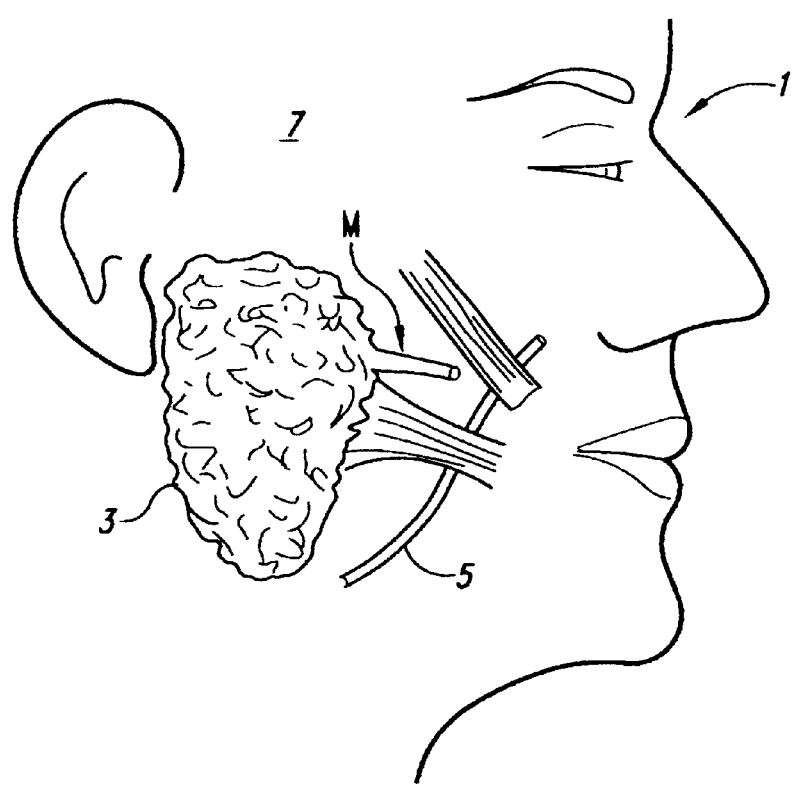
FIG. 1 is an interior to the surface tissue side view of the human face illustrating the relative location of the parotid saliva duct an the parotid vein further illustrating the relative position of the ears, eyes, and lips to the target surgical location.

Now referring to FIG. 1., the instant invention is a surgical method for the introduction of naturally-occurring saliva antibodies (not shown) directly into the bloodstream of the patient 1 by surgically directing the saliva flow 2 from a parotid saliva gland 3 into the blood 4 flowing in a selected parotid venal plexuses vein 5. There is a wide range of embodiments for the instant invention. Specifically, there are two principal embodiments for the location of the surgery, and several involving the type of surgical tee used.

The preferred embodiment is surgery to the outside surface of the face of the patient 1 using a surgical tee (not shown). Now referring to FIG. 2, the preferred method in either embodiment is to locate the area of the incision 23 using a light wand 9 or a strong source of hand held light such as a flashlight (not shown).

Figure 2:
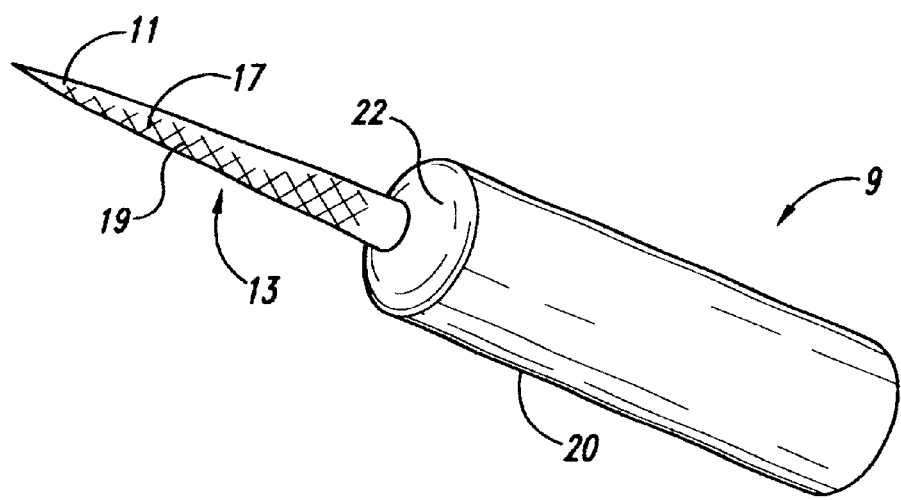
FIG. 2 is an isometric view of the light wand illustrating the probe and probe tip.
Figure 3:
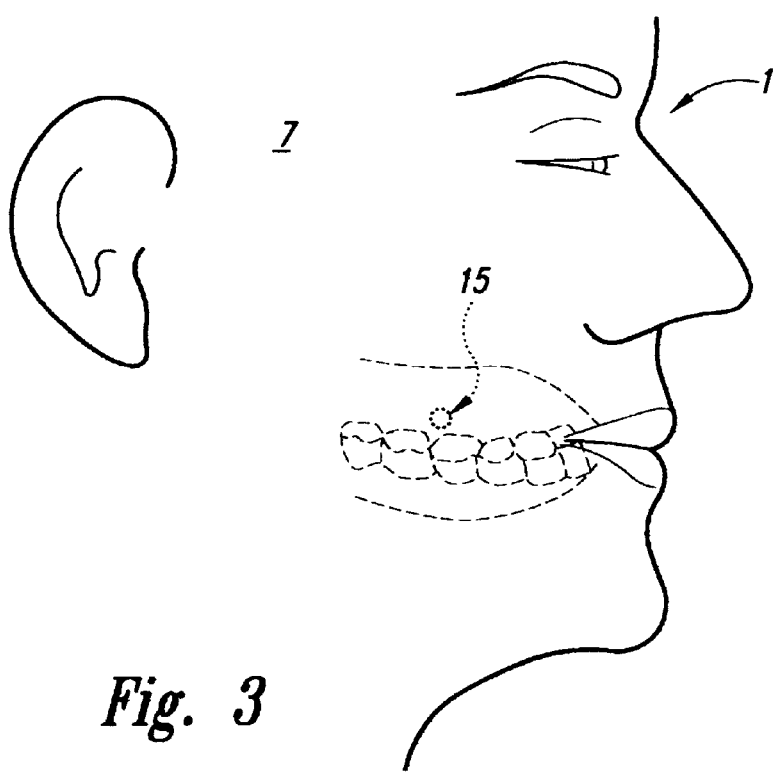
FIG. 3 is a side view of the human face illustrating the relative location of the parotid saliva duct opening into the oral cavity and further illustrating the relative position of the ears, eyes, and lips to saliva duct opening.

Now referring to FIG. 2 and FIG. 3, the tip 11 of the probe 13 of the light wand is inserted into the parotid duct opening 15 up to the insertion point 17 indicated on the probe. Light from the probe 13 is visible on the surface of the face or on the interior surface of the cheek (not shown). Surgery follows the following steps:

Step 1: Preoperative Procedures

The use of surgery to treat conditions internal to the tissue of the face is extremely well known in the art. The same preoperative procedures should be used as precedes any facial surgery. Consideration should be given to sterility of the operating form and the patient's 1 condition prior to the surgery. Unique to AIDS, due to the high concentration and occurrence in the undeveloped economic areas, is the need to perform this surgery in rural or even non-hygienic arenas. Following standard pre-surgical chemo-prophylactic treatment is always in order, but is not relevant to the instant invention.

Step 2: Locating the Surgical Area

Still referring to FIG. 2 and FIG. 3, the ideal location to perform the surgery on the face of the patient 1 should be located. To do this, the top 11 of the probe 13 of the light wand 9 is inserted into the opening 15 of the parotid saliva duct 19 up to the point 17 indicated on the probe 13 that is indicated by the patient's parameters.

The tip 11 of the probe 13 of the light wand 5 should be inserted far enough to illuminate the parotid saliva gland area 21. The parotid saliva duct 19 is specifically located with respect to veins in the immediate area and can be located by the light produced by the light wand probe 13 shining in the tissue of the face area of the cheek 21 once the skin is incised to the proximate depth of the parotid saliva duct 19.

The age and size of the patient should be considered. The diameter of the light wand probe 13 can be adjusted to the size of the expected parotid duct 5 of the patient. Children will have a parotid ducts 5 typically from ¹⁄₁₀ to ½ millimeters in diameter. Adults will have parotid ducts 5 typically from ½ to 1½ millimeters in diameter.

Figure 5:
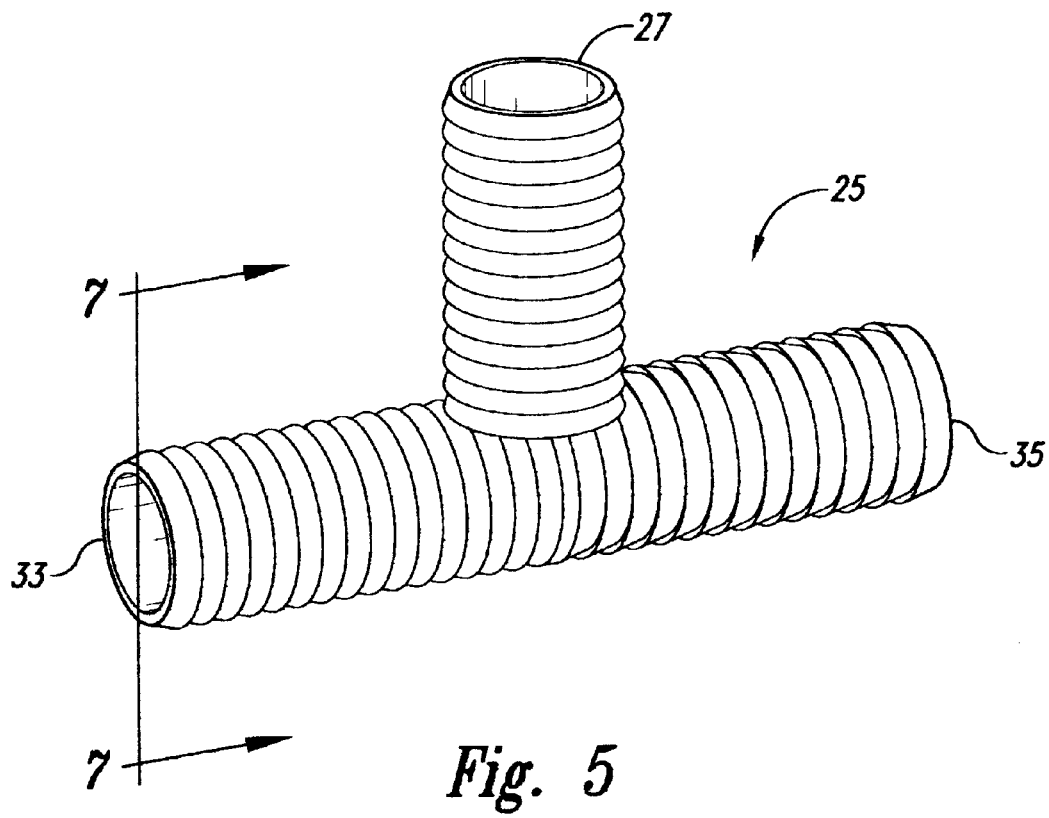
FIG. 5 is an isometric view of the surgical tee.

Now referring to FIG. 5, while the exact location of the incision 23 will vary somewhat in its exact location, the general location will be just anterior to the duct opening 15 and can be predicted without use of the light wand to a reasonable degree of accuracy.

The instant invention can be utilized without the light wand 9 in the event that it would become necessary. However, use of the light wand 9 can aid in reducing the size of the necessary incision 23 and the degree of skill required by the surgeon or skilled medical personnel, which is a highly desirable factor to the patient.

The light wand 9 is the most accurate known means to find the best location for the surgical incision. However, a flashlight (not shown) placed inside the mouth will in some cases be enough to locate the venal plexuses vein 5 and the parotid saliva duct 19.

Surgery can be performed either inter or intra-orally. The preferred embodiment is surgery to the exterior of the face 7. Interoral surgery will eliminate visible scarring, but creates other problems. Surgery inside the oral cavity is less sterile and more restricted in access. An additional disadvantage is that the interoral incision must pass through a muscle layer and has a greater probability of complications.

Step 3: Local Anesthesia

Figure 4:
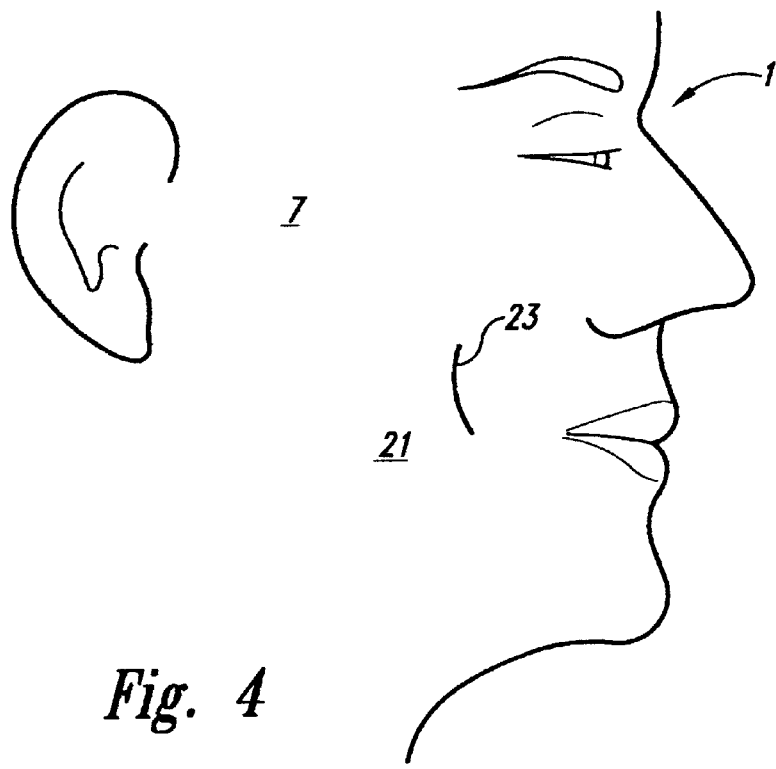
FIG. 4 is a side view of the human face illustrating the relative location of the incision relative to the ears, eyes, and lips.

Now referring to FIG. 4, the area of the incision 23 should be anaesthetized. This is typically done by using standard dental techniques using a 30 gage short needle and a cartridge of dental anesthetic in an aspirating dental syringe, injected at or anterior into the parotid duct 19. Use of anesthetic is well known in the art.

Step 4: Sterilization of Surgical Area

Still referring to FIG. 4, the area of the incision 23 should typically be sterilized using an iodine swab and is also well known in the art. Now referring to FIG. 5, the surgical tee 25 should also be sterilized prior to introduction into the patient 1. The surgical tee has a first end 33, second end 35, and a perpendicular end 27.

Step 5: Opening of Surgical Area

Referring to FIG. 4, the surgical area 21 should typically be opened with a #2 scalpel blade to create the incision 23. The incision 23 should be through the full thickness of the skin and carefully dissected posterior to any blood vessels, down into the parotid gland saliva duct 19, illuminated by the light wand 9. Now referring to FIG. 6, the parotid saliva duct 19 is then separated from the surrounding tissue with blunt dissection thereby forming a distal end 19a and a proximal end 19b.

Step 6: Removal of the Light Wand

The light wand 9 can be removed at this point, or it can be left in to assist the surgeon in identifying the parotid saliva duct 19 which is clear. Care is typically required in locating the parotid saliva duct 19. For most surgeries, it would be helpful to leave the light wand 5 in place at this step in the procedure. A strong internal light source, not shown, can be used to further illuminate the surgical area.

Step 7: Selection of Vein

Figure 6:
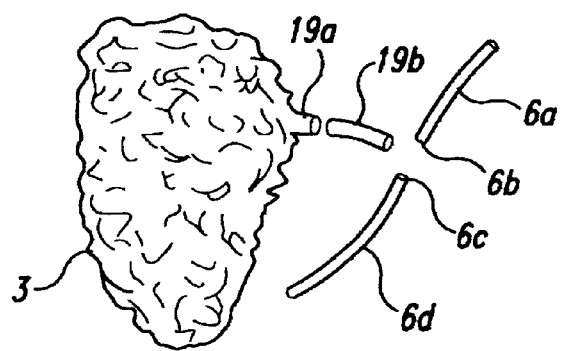
FIG. 6 is an isometric view showing the relative view of the points of insertion of the surgical tee into the parotid saliva duct and the parotid venal plexuses vein.

Still referring to FIG. 6, within the surgical area 21 in an area exposed by the incision 23, a parotid venal plexuses vein 5 should be selected and isolated by blunt dissection in the area anterior to the incision 23. The portion of the parotid plexuses vein 5 should be one that is in close proximity to the parotid saliva duct 19. Severing the parotid venal plexuses vein 5 creates a first vein end 6a and a second vein end 6b. The first vein end 6b having a first vein opening an the second vein end 6c having a second vein opening 6d.

Now referring again to FIG. 5, enough area around the parotid venal plexuses vein 5 should be clear enough to enable the insertion of a surgical tee 25 or other connection means between the parotid venal plexuses vein 5 and the parotid saliva duct 19.

Step 8: Severing of the Parotid Saliva Duct

If not already removed, the light wand 9 should be removed at this point. The parotid saliva duct 19 is severed at this time using a suture scissors (not shown) forming a distal end 19a and a proximal end 19b. The point of severing the parotid duct should be as far anterior as possible.

Step 9: Insert Connector into Parotid Duct

Now referring to FIG. 5 and FIG. 6, in the preferred embodiment, the next step is to insert the third tee end 27 of the tee 25 into the proximal end 19a of the parotid saliva duct 19 and occlude the distal end 19b of the parotid saliva duct 19 using standard surgical procedures such as cauterization, suturing, clamping, or cyanoacrylate type adhesive. The method of occluding is not relevant to the instant invention.

Step 10: Sever Selected Vein

Still referring to FIG. 6, double clamp the vein lateral to and before severing ends 6a and 6b of the selected parotid plexuses vein 5. Sever the parotid plexuses vein 5 between the clamps forming the first vein opening 6c and the second vein opening 6d.

Step 11: Connection of Vein and Parotid Duct

Insert the first tee end 33 and the second tee end 35 of the tee into the severed ends of the plexus vein at 6c and 6d. Next, secure the ends of the vein to the surgical tee 25 using standard surgical procedures such as suturing, clamping, or cyanoacrylate adhesive. At this point, the saliva produced by the parotid saliva gland 3 can enter into the blood flowing through the parotid plexus vein 5.

It should be noted that it is not material to the invention whether the duct connections or the vein connections are made first.

Step 12: Close Incision

The final step in the surgical procedure is to remove the clamps and check for leakage of fluids from either the vein 5 or duct 19 connections. Once no leakage is confirmed, then the incision is closed with sutures such as 000 silk or absorbable sutures which are well known in the art.

Step 13: Post Operative Procedure

Any opening of the human body requires postoperative care. This is well known in the art and is not relevant to the instant invention. Typically, the sutures should be removed in five to seven days. Any signs of infection should be treated by medically-trained personnel.

ALTERNATIVE MEANS OF DUCT-VEIN CONNECTIONS

The preferred embodiment described above is the preferred means to connect the parotid venal plexus vein 5 to the parotid saliva duct 19. However, other embodiments are possible. One such embodiment is the use of sewing the exposed ends of vessels and duct together in the common method that is well known in the art.

Use of Serrated Surgical Tee

Figure 7:
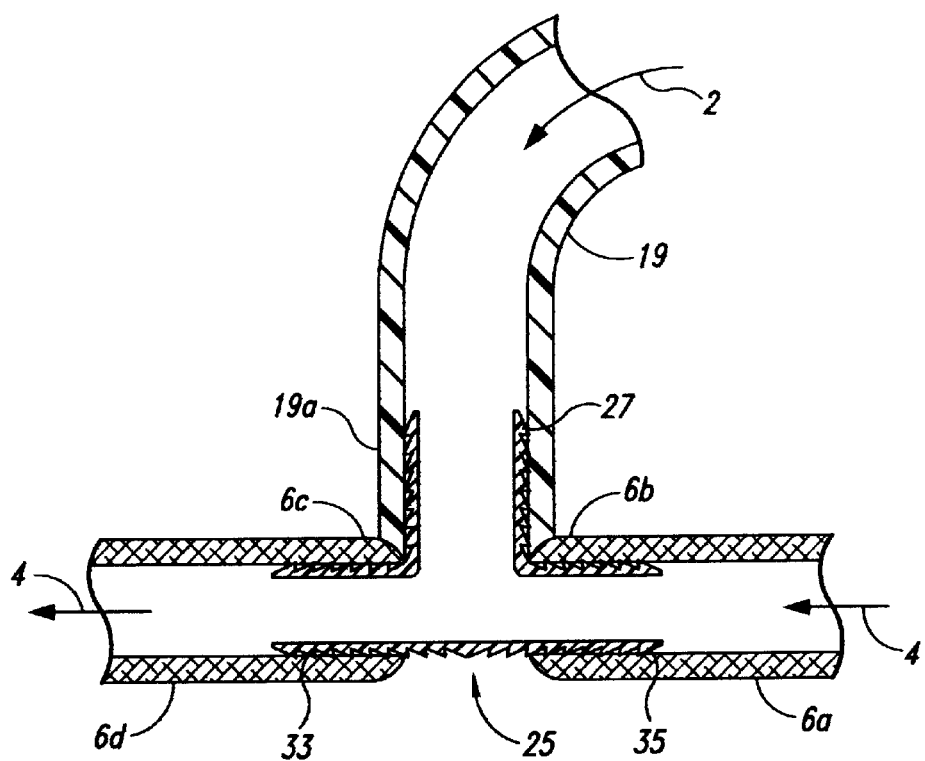
FIG. 7 is a cross-sectional view of the serrated edge surgical tee embodiment along lines 7—7.

Now referring to FIG. 7, another embodiment is the use of a serrated surgical tee 25 whose outer surfaces are covered with serrated edges that are sloping toward the surgical tee's 25 center area. These edges will facilitate the holding of the ends of the parotid venal plexus vein onto the serrated surgical tee 25. Depending upon what is needed, any of the surgical tee ends 27,33,35 can be serrated or unserrated. Once inserted, the sewing or gluing should still be used.

Cut and Glue Method

Figure 8:
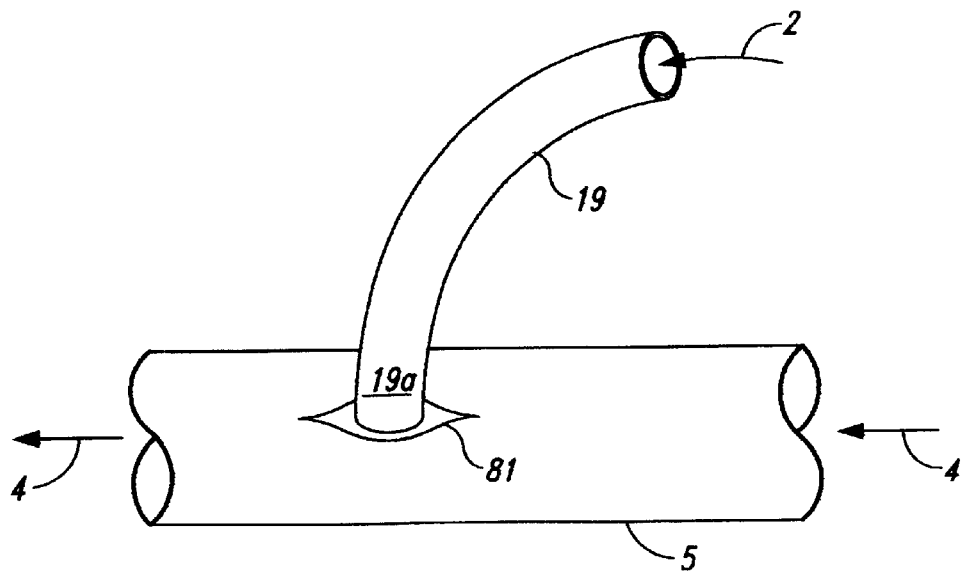
FIG. 8 is an isometric view of the "cut and glue" embodiment.

Now referring to FIG. 8, yet another embodiment of the instant invention is using sewing or glue without a surgical tee 25. The parotid venal plexus vein 5 is incised creating a vein opening 81 to the approximate diameter of the parotid saliva duct 19, and the proximal end 19a is inserted into the vein opening 81. The distal end 19a of the parotid saliva duct 19 is then fixed into the parotid venal plexus vein 5 using sewing or glue or any other commonly-used procedure that is known in the art.

Insertion Tee Embodiment

Figure 9:
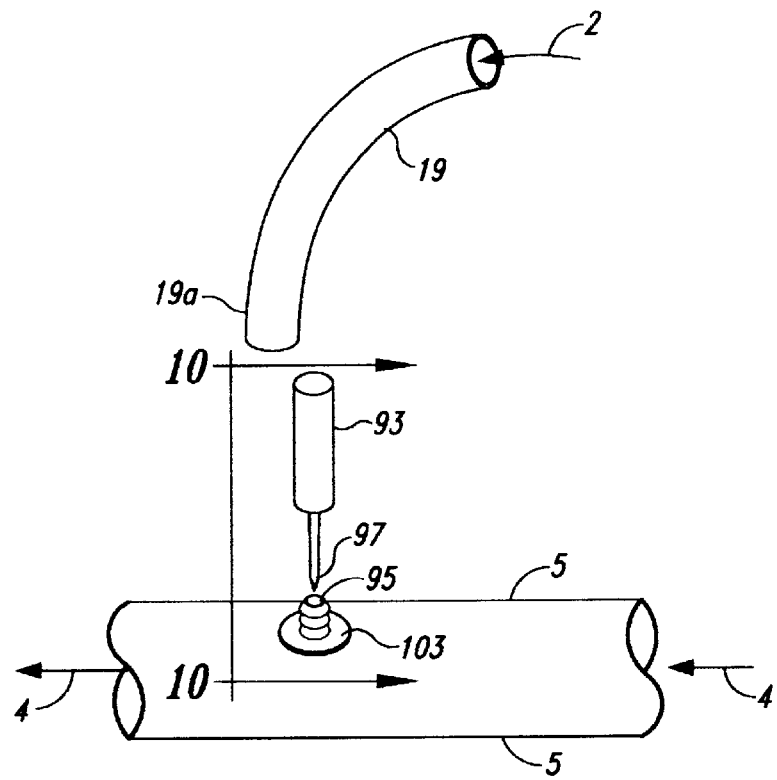
FIG. 9 is an isometric view of the puncture surgical tee embodiment.
Figure 10:
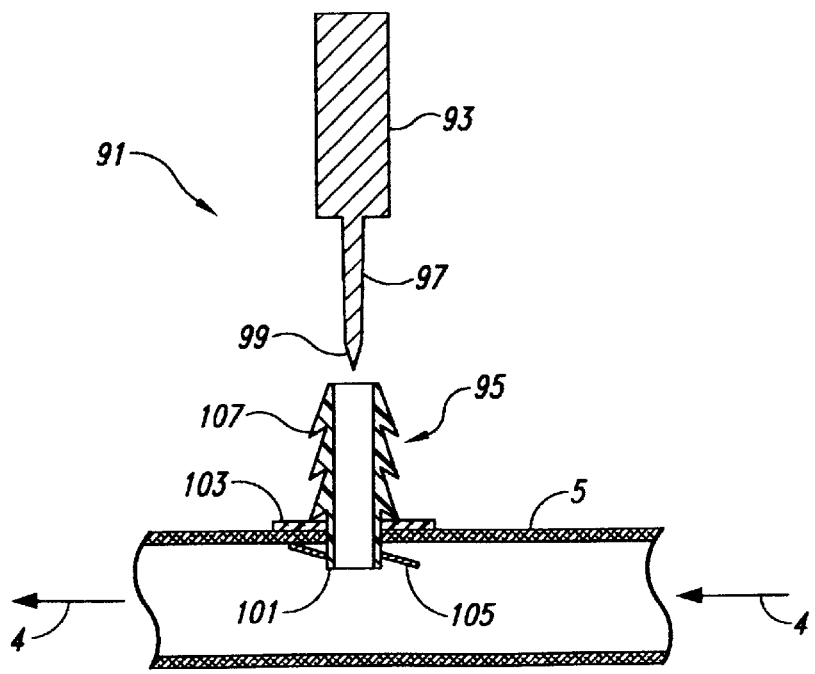
FIG. 10 is a cross sectional view of an insertion plug embodiment of the surgical tee along lines 10—10.

Now referring to FIG. 9 and FIG. 10, the insertion tee embodiment is illustrated. The insertion tee 91 has three parts: the plunger 93, the serrated screw attachment 95, and the lance 97, having a penetrating tip 97 which has a sharp tip 99. To use the insertion tee 91, the plunger 93 is inserted into the serrated screw attachment 95 to the point of full insertion. When the plunger 93 is fully inserted, a sharp tip 99 will protrude from the vessel end 101 of the insertion tee 91. The medical personnel performing the procedure will push the sharp tip 99 into parotid venal plexus vein 5.

Once the parotid venal plexus vein 5 is punctured, the serrated screw attachment 95 will be rotated until the flange 103 rests snugly against the parotid venal plexus vein 5 surface. The preferred method in use of the insertion tee 91 is to use threading 105 as in a common wood or metal screw, to made the flange 103 fit snugly again the venal plexus vein 5. The threading 105 of the serrated screw attachment 95 will affix the insertion tee 91 into the parotid venal plexus vein 5 up to the point of the flange 103.

Once in place, the serrated tee 25 can be placed into the blunt dissected end of the parotid duct 19a and sealed in place using standard surgical procedures. The serrated edges 107 of the serrated screw attachment facilitates sealing the parotid duct 5 to the surgical tee 25.

Other Tee Embodiments Possible

Additionally, other embodiments are possible such as the use of different materials. Whatever materials that are used must be biocompatible and not cause blood clotting. Expected composition of surgical tees includes plastics, ceramics, and metals such as stainless steel or titanium embodiments.

LIGHT WAND CONSTRUCTION

Now referring to FIG. 2, the light wand 9 needs to be readily portable and capable of being held in the hand of the medical personnel utilizing the instant invention. The light wand body 20 of the light wand 9 should contain a power source such as batteries. The production of light from a hand held power source is similar to that of a common flashlight or fiber optic light and is well known in the art.

Out of the forward end 22 of the light wand body 20, a probe 13 will extend approximately the length of distance from the forward end 22 of the light wand body 20 when held near the mouth, approximately three to five centimeters beyond the expected location of the parotid duct opening 15. The probe should be constructed of light conductive material such as fiber-optic materials. The tip of the probe 11 should be rounded and tapered to allow for easy insertion of the probe and to allow for naturally-occurring variances in parotid duct size. Also, from the insertion point 17 to the tip 11 could be frosted so that light leaves the frosted area 19 well as the tip 11.

In the more isolated areas, commonly-used luminescent materials such as phosphorous latent plastic can be used as a probe 11 instead of a power-generated light source. Proper care should be taken to ensure sterility and non-contamination of the patient 1.

SALIVA PRODUCTION REQUIREMENTS

Obviously, for the instant invention to work, there must be adequate saliva production. The production of saliva depends upon many factors. For example, AIDS itself inhibits the production of saliva. Other medical conditions such as diabetes, other diseases and advanced age can reduce the amount of saliva that is produced by the patient 1. Also, the maximum amount of saliva is produced when the patient is sitting or eating.

AIDS limits the amount of saliva produced in the later stages. Therefore, the earlier the instant invention is used once AIDS is detected, the more benefit it should be expected to be. Consequently, in the later stages of AIDS, conventional medication should be used to stabilize the patient prior to the surgery being conducted.

OTHER EMBODIMENTS POSSIBLE

While several embodiments of the present invention have been shown and described, it will be apparent to those skilled in the art that many changes and modifications may be made without departing from the invention in its broader aspects.

I claim:

1. A method for the surgical treatment of blood-borne infectious diseases wherein saliva-borne antibodies are introduced into the bloodstream of the patient by:

severing the parotid saliva gland duct forming a proximal end and a distal end;

making an incision into the parotid venal plexuses vein;

inserting the proximal end of the parotid saliva duct into the incision; and sealing the parotid venal plexuses vein around said parotid saliva duct and sealing off the distal end of said parotid saliva duct, whereby said saliva-borne antibodies are introduced into the bloodstream of the patient to treat said infectious disease.

2. The method in claim 1 wherein the sealing means is an adhesive.

3. The method in claim 2 wherein the sealing means is cyanoacrylate type adhesive.

4. The method in claim 1 wherein the sealing means is sewing.

5. A method for the surgical treatment of blood-borne infectious diseases wherein saliva-borne antibodies are introduced into the bloodstream of the patient by:

determining the location of the surgery by use of a light source;

severing the parotid saliva gland duct forming a proximal end and a distal end;

making an incision into the parotid venal plexuses vein;

inserting the proximal end of the parotid saliva duct into the incision; and sealing the parotid venal plexuses vein around said parotid saliva duct and sealing off the distal end of said parotid saliva duct, whereby said saliva-borne antibodies are introduced into the bloodstream of the patient to treat said infectious disease.

6. The method in claim 5 wherein the light source is a light wand that is inserted into the parotid saliva duct.

7. A method for the surgical treatment of infectious diseases wherein saliva-borne antibodies are introduced into the bloodstream of the patient by:

severing the parotid saliva gland duct forming a proximal end and a distal end;

severing the parotid venal plexuses vein forming a first opening and a second opening;

inserting the proximal end of the parotid saliva duct into the perpendicular end of a surgical tee, and Inserting a first tee end into said first vein opening, and Inserting a second tee end into said second vein opening sealing the parotid venal plexuses vein and proximal end of the parotid saliva duct in place using an adhesive, sealing off said distal end, whereby said saliva-borne antibodies are introduced into the bloodstream of the patient for the treatment of said infectious disease.

8. The method in claim 7 wherein the surgical tee is constructed of materials selected for the groups comprising plastic, ceramic, and metal.

* * * * *